(12) United States Patent
Bogatzki et al.

(10) Patent No.: US 11,298,185 B2
(45) Date of Patent: Apr. 12, 2022

(54) OPTICAL FIBER WITH MODIFIED DISTAL END

(71) Applicant: LEONI Kabel GmbH, Roth (DE)

(72) Inventors: Angelina Bogatzki, Berlin (DE); Patrick Stock, Berlin (DE)

(73) Assignee: LEONI Kabel GmbH, Roth (DE)

( * ) Notice: Subject to any disclaimer, the term of this patent is extended or adjusted under 35 U.S.C. 154(b) by 309 days.

(21) Appl. No.: 16/124,930

(22) Filed: Sep. 7, 2018

(65) Prior Publication Data
US 2020/0078092 A1 Mar. 12, 2020

(51) Int. Cl.
*A61B 18/22* (2006.01)
*G02B 6/02* (2006.01)

(52) U.S. Cl.
CPC .............. *A61B 18/22* (2013.01); *G02B 6/02* (2013.01); *A61B 2018/2205* (2013.01); *A61B 2018/2244* (2013.01); *A61B 2018/2288* (2013.01)

(58) Field of Classification Search
CPC combination set(s) only.
See application file for complete search history.

(56) References Cited

U.S. PATENT DOCUMENTS

| | | |
|---|---|---|
| 8,073,297 B2 | 12/2011 | Griffin |
| 8,152,718 B2 | 4/2012 | Cheng |
| 8,285,097 B2 | 10/2012 | Griffin |
| 8,358,890 B2 | 1/2013 | Zerfas et al. |
| 8,425,500 B2 | 4/2013 | Hanley et al. |
| 8,532,456 B2 | 9/2013 | Hixon |
| 8,644,666 B2 | 2/2014 | Hixon |
| 8,861,907 B2 | 10/2014 | Zerfas et al. |
| 9,050,118 B2 | 6/2015 | Hanley et al. |
| 9,122,009 B1 | 9/2015 | Griffin |
| 9,207,402 B2 | 12/2015 | Zerfas et al. |
| 9,223,089 B1 | 12/2015 | Griffin |
| 9,289,262 B2 | 3/2016 | Hanley et al. |
| 9,820,638 B2 | 11/2017 | Cheng |
| 9,968,403 B2 | 5/2018 | Hasenberg et al. |
| 2002/0049435 A1* | 4/2002 | Mersch .............. G02B 6/0008 606/15 |
| 2014/0058368 A1 | 2/2014 | Hogue |
| 2016/0081749 A1 | 3/2016 | Zhang et al. |
| 2016/0157920 A1* | 6/2016 | Vayser .............. A61B 18/1402 600/249 |
| 2017/0135767 A1 | 5/2017 | Zerfas et al. |
| 2017/0172658 A1* | 6/2017 | Zipper .................... A61N 5/06 |
| 2018/0000645 A1* | 1/2018 | Scheller ............. A61F 9/00823 |

(Continued)

FOREIGN PATENT DOCUMENTS

WO WO 2011/063074 5/2011

OTHER PUBLICATIONS

International Search Report and Written Opinion issued in the corresponding International Application No. PCT/IB2019/000992 dated Feb. 6, 2020.

(Continued)

*Primary Examiner* — Shirley X Jian
(74) *Attorney, Agent, or Firm* — Haug Partners LLP

(57) ABSTRACT

An Optical fiber with modified distal end and related methods are provided. The optical fiber extends from a proximal end portion to a distal end portion and includes a core, a cladding, a coating, and an optional jacket. The distal end portion comprises a portion with an enlarged outer diameter.

31 Claims, 2 Drawing Sheets

(56) References Cited

U.S. PATENT DOCUMENTS

2018/0042677 A1   2/2018  Yu et al.
2018/0078311 A1*  3/2018  Scheller .............. A61F 9/00823

OTHER PUBLICATIONS

AccuTrac™, Single-Use Holmium Laser Fiber; Flexiva TracTip™, High Power Single-Use Laser Fiber; Designed for reliable, one-step passage through a deflected ureteroscope.
LaseGuide™ NAV, Surgical Laser Fiber.
ProFlex® Holmium Laser Fiber.

* cited by examiner

OPTICAL FIBER WITH MODIFIED DISTAL END

FIELD OF THE INVENTION

This disclosure relates generally to optical fibers, methods of making optical fibers, and their methods of use. In particular, this disclosure relates to optical fibers with a modified distal end.

BACKGROUND OF THE INVENTION

Optical fibers have been implemented for a variety of light transmitting purposes. For example, optical fibers are well known for transmitting light from a light source to a delivery location. Such fibers may be implemented in a fiber-optic communication system to deliver light from a source (e.g., a cable provider) to a destination (e.g., a user's set-top box).

Optical fibers as also well known for use in the medical field. For example, in order to ablate a kidney (or bladder) stone a doctor may insert an endoscope or catheter into a patient's urinary tract. An optical fiber may be fed through the endoscope/catheter to a location proximate to the stone. Radiation, typically from a holmium (Ho) laser, is directed through the optical fiber and onto the stone. The energy from the radiation is configured to break the stone into smaller pieces or cause the stone to disintegrate.

Typical optical fibers used with catheters/endoscopes in these types of urology procedures have a distal end (i.e., the end fed through the endoscope) with a planar face (i.e., tip). Since the distal end is often created from cutting the optical fiber, the distal tip of the optical fiber has a sharp edge around its periphery. When feeding such an optical fiber through the endoscope/catheter the sharp edge may damage an inner surface of the endoscope/catheter, and complementarily, the inner surface of the endoscope/catheter may damage the distal end of the optical fiber. Moreover, the sharp edge makes it more difficult for a practitioner to feed the optical fiber through the endoscope, especially if significant bending is necessary to place the endoscope/catheter, and thus the optical fiber, in proximity to a target site (e.g., the location of a kidney stone).

Certain prior art devices attempt to address the above problems by providing an optical fiber with a rounded or polished distal tip (e.g., LaseGuide™ Nav Fiber by LP Surgical Fibers, ProFlex® by Bard, and GentleFlex™ by Boston Scientific). Although the rounded distal tip may help to prevent damage, the distal tip of these fibers still makes contact with an inner lumen of the endoscope. Such contact, consequently, leads to unwanted damage to the optical fiber (or catheter/endoscope) and may make it difficult feed the fiber to the desired location. Additionally, such prior art devices are not of a unitary construction, and instead splice on the distal tip, which creates instabilities in the optical fiber and increases manufacturing costs.

Thus, there is a need to address the problems associated with optical fibers.

SUMMARY OF THE INVENTION

Various illustrative embodiments of the present disclosure provide a modified optical fiber and related methods. In accordance with an aspect of an illustrative embodiment of the present disclosure, the optical fiber extends from a proximal end portion to a distal end portion. The distal end portion may include sections with differing outer diameters that create a "snakehead" shape.

The distal end portion of the optical fiber may include a first section, a second section, and a distal tip. The first section may be located between and abut the proximal portion and the second section. The second section may be located between and abut the first section and the distal tip.

According to embodiments, the optical fiber comprises: a core; and a cladding disposed on the core; wherein the optical fiber extends from a distal portion to a proximal portion and includes a longitudinal axis, and wherein the distal portion comprises: a first section; and a second section, wherein at least one of the first section and the second section comprises an outer diameter that is greater than the outer diameter of the proximal portion.

The first section may have an outer diameter that increases along at least a part of its length from the proximal portion to the second section. The increase in diameter may range from approximately 20% to 100% of the outer diameter of the proximal portion of the fiber. Thus, the first section includes at least a portion with a diameter that is approximately equal to 120% to 200% of the outer diameter of the proximal portion. According to alternative embodiments, the increase in diameter may range from approximately 20% to 60% of the outer diameter of the proximal portion of the fiber. According to further embodiments, the increase in diameter may range from approximately 30% to 60% of the outer diameter of the proximal portion of the fiber. According to still further embodiments, the increase in diameter may range from approximately 50% to 60% of the outer diameter of the proximal portion of the fiber.

The length of the first section may be approximately 250 μm to 600 μm. According to alternative embodiments, the length of the first section may be approximately 350 μm to 500 μm. According to further embodiments, the length of the first section may be approximately 400 μm.

According to embodiments, the second section may have an outer diameter that decreases along at least a part of its length from the first section to the distal tip. The decrease in outer diameter may range from approximately 20% to 50% of the maximum outer diameter of the first section. Thus, the second section may include at least a portion with an outer diameter that is approximately equal to the outer diameter of the proximal portion and at least a portion with a outer diameter that is approximately equal to the maximum outer diameter of the first section. According to alternative embodiments, the decrease in diameter may range from approximately 30% to 60% of the maximum outer diameter of the first section. According to further embodiments, the decrease in diameter may range from approximately 50% to 60% of the maximum outer diameter of the first section. According to alternative embodiments, the outer diameter of the second section may be equal to the maximum outer diameter of the first section.

The length of the second section may be approximately 250 μm to 600 μm According to alternative embodiments, the length of the second section may be approximately 350 μm to 500 μm. According to further embodiments, the length of the second section may be approximately 400 μm.

The first section and the second section may create an arcuate, semicircular, or parabolic shape on the distal end portion of the optical fiber. According to alternative embodiments, the first section and the second section may create other shapes on the distal end portion of the optical fiber, for example, a trapezoidal shape.

According to embodiments according to the above configuration, the distal portion of the optical fiber may have a length of approximately 500 µm to 1200 µm. A first section (e.g., the proximal half) may have an outer diameter that increases from a diameter $D_1$, which is the approximate outer diameter of the proximal portion, to an outer diameter $D_2$, which is approximately 120% to 200% of $D_1$. A second section (e.g., the distal half) may have an outer diameter that decreases from diameter $D_2$ to an outer diameter approximately equal to $D_1$. According to the rate at which the first section's diameter increases and the rate at which the second section's diameter decreases, the distal portion includes a cross-sectional profile (along the longitudinal axis) that has a snakehead-like shape, parabolic shape, arcuate shape, semi-circular shape, trapezoidal shape, or the like.

According to embodiments, the distal tip of the optical fiber may include a curved portion and a planar portion. The curved portion in combination with the planar portion may be shaped such that the distal tip does not include any sharp edges. According to alternative embodiments, the distal tip of the optical fiber may include a substantially curved or flat surface. According to further embodiments, the distal tip may take other shapes.

The outer diameters and shapes of the first section, second section, and distal tip are such that the distal end portion of the optical fiber includes a thickened area that is located proximally from the distal tip by a distance, creating a distal end with a snakehead-like shape.

According to embodiments, the optical fiber may be a silica fiber comprising a core, a cladding, a coating, and an optional jacket. The core and cladding may be entirely made from silica. The coating may made from silicone or hard clad. The optional jacket may be made from ethylene tetrafluoroethylene (ETFE) of Nylon.

The core may extend from the proximal end to the distal end of the optical fiber. The coating may be deposited or disposed on the cladding. The jacket may be disposed or deposited on the coating.

In accordance with an aspect of another illustrative embodiment of the present disclosure, methods of fabricating an optical fiber with a modified distal end are disclosed. The method may include heating a distal end of the optical fiber with a heating element, for example, an arc lamp. Heat from the heating element may be configured to deform the distal end at the locations of the first section and second section. The heat may be varied across the distal end of the optical fiber to create a snakehead-like shape. According to embodiments, the heating element is brought in close proximity to the distal end of the optical fiber. The optical fiber may then undergo controlled rotation and/or movement so that the distal end deforms (e.g., due to melting and surface tension properties). According to alternative embodiments, pressure may be applied to the distal end of the optical fiber (e.g., during a manufacturing process) in order to deform the distal end. According to further embodiments, a capillary ring may be attached to the distal end of the optical fiber in order to form the modified shape.

In accordance with an aspect of another illustrative embodiment of the present disclosure, an optical fiber with a modified distal end is associated with a catheter or endoscope for use in a urology procedure. The endoscope or catheter may be fed into the body of a patient, for example, by way of a guide wire such that the endoscope or catheter is located proximate to a renal or bladder stone. The optical fiber may be fed through the endoscope or catheter such that the distal tip of the optical fiber is also located proximate to the rental or bladder stone.

An energy source (e.g., a holmium laser) may be coupled to the proximal end of the optical fiber. When the energy source is activated, light from the energy source travels through the optical fiber and is focused, in a direction along the longitudinal axis of the optical fiber, out of the distal tip and onto the stone. The energy is focused through the optical fiber in order to break the stone into smaller pieces or cause the stone to disintegrate. The smaller pieces may then be removed by known means. Additionally, due to the snakehead shape of the optical fiber the beam profile may be concentrated (e.g., focused) to a higher degree, as compared to traditional flat tip optical fibers. Such focusing further helps to break the stone with a lower power energy source, which advantageously increases the life span of an optical fiber of the present disclosure.

Due to the shape of the modified distal end of the optical fiber, portions of the first and/or second sections make contact with an inner lumen of the catheter or endoscope when the optical fiber is fed there through. Additionally, the shape of the modified distal end helps prevent the distal tip and at least a portion of the distal end (e.g., a portion of the second section) of the optical fiber from making contact with the inner lumen of the catheter or endoscope. Additionally, because a larger surface area of the distal end of the modified optical fiber makes contact with the inner lumen, a greater degree of stability is achieved during placement of the fiber within the body.

Since an intermediate portion (e.g., portions of the first and/or section section) of the optical fiber of the present disclosure has an increased diameter relative to the rest of the fiber, the distal tip is protected from making contact with the inner lumen of the catheter or endoscope during placement within a patient. By preventing the distal tip from making contact with the inner lumen, the distal tip is protected from being damaged by the catheter or endoscope. For example, many catheters or endoscopes have a metallic inner lumen through which an optical fiber is fed. Due to necessary bending of the catheter or endoscope for placement (e.g., within a kidney), the distal tip of the optical fiber often makes contact with the metallic inner lumen as it is fed through the catheter or endoscope. Such contact causes damage to the distal tip of the optical fiber (or to the inner lumen of the catheter or endoscope), which often requires the fiber (or endoscope/catheter) to be replaced. Such a replacement is costly and may also delay the procedure. By having an optical fiber with thicker portion (i.e., a larger diameter) located a distance away from the distal tip; the distal tip is prevented from making contact with the inner lumen, thus preventing damage to the distal tip.

According to embodiments, a method of performing a urology procedure, comprises: inserting an endoscope or catheter through a vessel lumen of a patient; feeding the endoscope or catheter through the vessel until a distal end of the endoscope or catheter is located proximate to a renal or bladder stone; inserting an optical fiber into a channel located within the endoscope or catheter, wherein the optical fiber includes a distal portion, a proximal portion, and a distal tip, the distal portion further including a section have a larger outer diameter than the diameter of the proximal portion and the distal tip; feeding the optical fiber through the channel located within the endoscope or catheter until the distal tip of the optical fiber is located proximate to the stone, wherein the section of the distal portion having a larger outer diameter contacts an inner wall of the channel and prevents the distal tip from contacting the inner wall.

BRIEF DESCRIPTION OF THE DRAWINGS

The following description, given by way of example and not intended to limit the invention to the disclosed details, is

FIG. 2a is a longitudinal, cross-sectional view of an embodiment of an optical fiber of the present disclosure with light being irradiated there through;

DETAILED DESCRIPTION

Detailed embodiments of the present optical fiber and methods are disclosed herein; however, it is to be understood that the disclosed embodiments are merely illustrative of an optical fiber, and methods that may be embodied in various forms. In addition, each of the examples given in connection with the various embodiments of the systems and methods are intended to be illustrative, and not restrictive. Further, the drawings and photographs are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present light emitting system, and methods.

Figure 1:
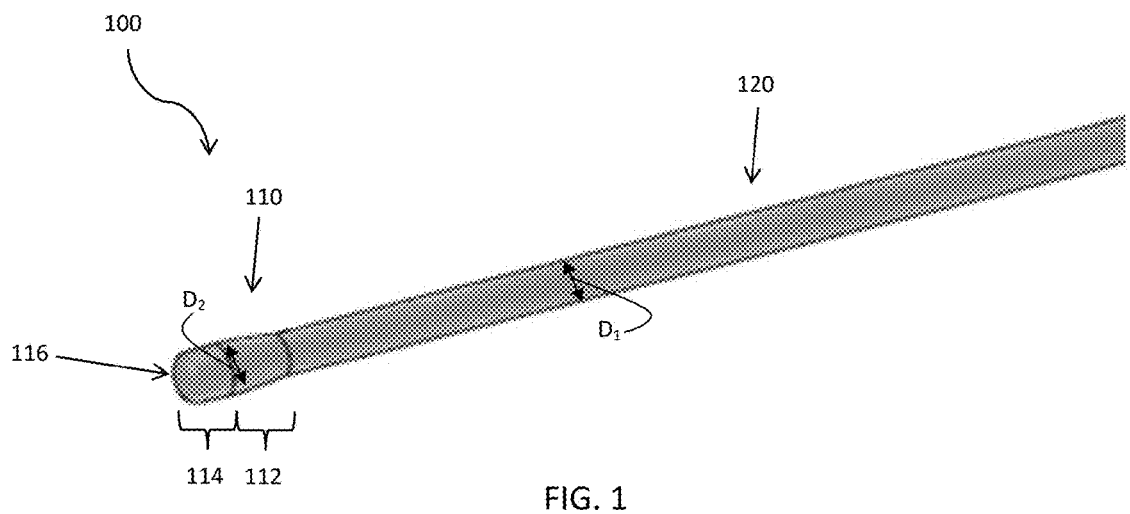
FIG. 1 is a perspective view of an embodiment of an optical fiber of the present invention.
Figure 2A:
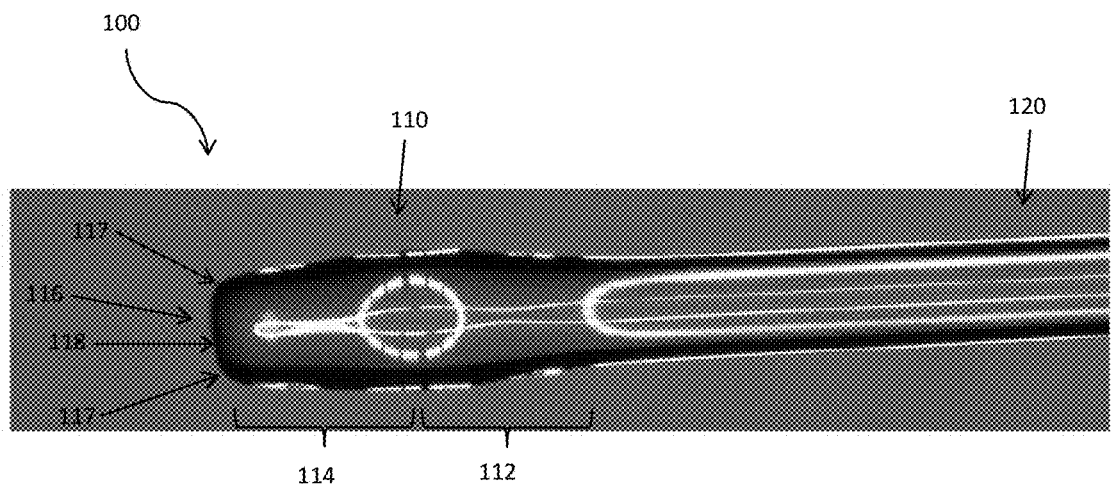
Figure 2B:
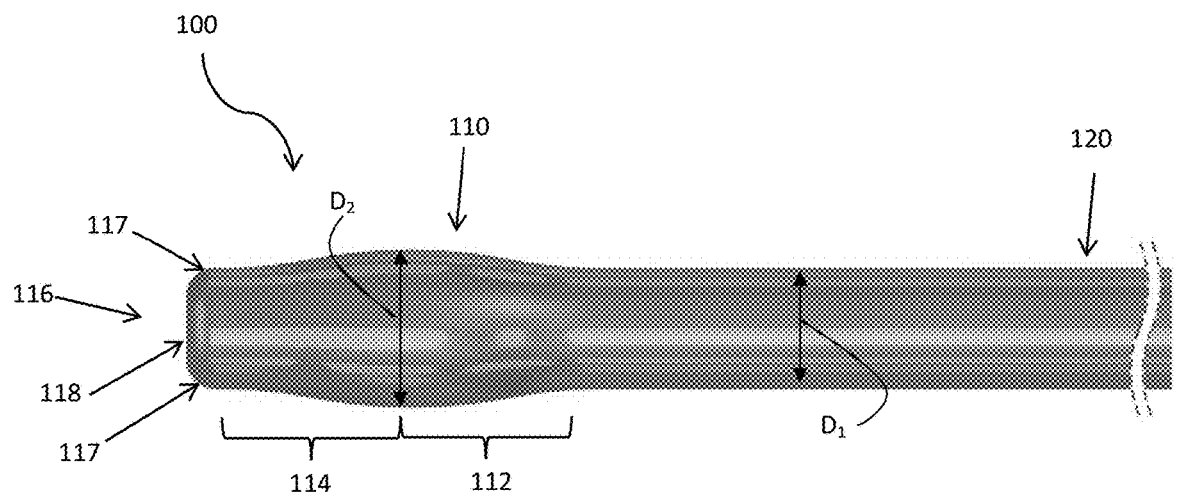
FIG. 2b is a longitudinal view of an embodiment of an optical fiber of the present disclosure.

With reference to FIGS. 1 and 2, an embodiment of an optical fiber 100 of the present disclosure is illustrated. The optical fiber 100 may include a core, a cladding, a coating, and an optional jacket. The optical fiber extending from a distal portion to a proximal portion and including a longitudinal axis, and wherein the distal portion comprises: a first section; and a second, wherein at least one of the first section and the second section comprises an outer diameter that is greater than the outer diameter of the proximal portion. The illustrative embodiments of FIGS. 1 and 2 are non-limiting and optical fibers within the scope of this disclosure may be modified.

According to an embodiment, optical fiber 100 may be an all silica fiber. Methods of manufacturing the fiber, which are described in more detail below, may result in the creation of an optical fiber with a modified distal end having a snakehead-like shape. The optical fiber may be configured to focus light passed through the core, such that light emitted from the distal tip is concentrated.

With further reference to FIGS. 1 and 2, optical fiber 100 may include a distal end portion 110 and a proximal end portion 120, the optical fiber extending from distal end portion 110 to proximal end portion 120. As further described below, distal end portion 110 includes a first section 112, a second section 114, and a distal tip 116.

The first section 112 may be located between and abut the proximal portion 120 and the second section 114. The second section may 114 be located between and abut the first section 112 and the distal tip 116.

According to embodiments, proximal portion 120 has an outer diameter $D_1$. The first section 112 may have an outer diameter that increases along its entire length from the proximal portion 120 to the second section 114, resulting in an outer diameter of $D_2$, where $D_2 > D_1$. The increase in diameter may range from approximately 20% to 100%, of the outer diameter of the fiber such that $D_2$ is approximately equal to 120% to 200% of $D_1$. According to preferred embodiments, the increase in diameter may range from approximately 30% to 60%. According to further embodiments, the increase in diameter may range from approximately 50% to 60%. The increase in diameter may be constant along the length of first section 112. According to alternative embodiments, the increase in diameter may be non-constant along the length of first section 112 (e.g., the diameter may increase logarithmically, exponentially, etc.). According to further embodiments, first section 112 may have a first portion that increases in diameter and a second portion with a constant outer diameter. The length of the first section may be approximately 250 μm to 600 μm. According to alternative embodiments, the length of the first section may be approximately 350 μm to 500 μm. According to further embodiments, the length of the first section may be approximately 400 μm.

According to embodiments, the second section 114 may have an outer diameter that decreases along its entire length from the first section 112 to the distal tip 116, wherein the decrease in diameter along the longitudinal axis of the section portion includes a decrease from $D_2$ to approximately $D_1$. The decrease in diameter may range from approximately 20% to 50%, of the maximum outer diameter of the first section. Thus, the second section includes at least a portion with an outer diameter that is approximately equal to the outer diameter of the proximal portion and at least a portion with a outer diameter that is approximately equal to the maximum outer diameter of the first section. According to alternative embodiments, the decrease in diameter may range from approximately 30% to 60% of the maximum outer diameter of the first section. According to further embodiments, the decrease in diameter may range from approximately 50% to 60% of the maximum outer diameter of the first section. According to alternative embodiments, the outer diameter of the second section may be constant and approximately equal to the maximum outer diameter of first section 112. According to further embodiments, the decrease in diameter may be non-constant along the length of second section 114 (e.g., the diameter may decrease logarithmically, exponentially, etc.). According to still further embodiments, second section 114 may have a first portion with a constant outer diameter and a second portion with an outer diameter that decreases. The length of the second section 114 may be approximately 250 μm to 600 μm According to alternative embodiments, the length of the second section may be approximately 350 μm to 500 μm. According to further embodiments, the length of the second section may be approximately 400 μm.

First section 112 and second section 114, in combination, may create an arcuate, semicircular, or parabolic shape on the distal end portion of the optical fiber (see FIGS. 1 and 2). According to alternative embodiments, the first section and the second section may create other shapes on the distal end portion of the optical fiber, for example, a trapezoidal shape.

According to embodiments according to the above configuration, the distal portion of the optical fiber may have a length of approximately 500 μm to 1200 μm. First section 112 (e.g., the proximal half) may have an outer diameter that increases from a diameter $D_1$, which is the approximate outer diameter of the proximal portion, to an outer diameter $D_2$, which is approximately 120% to 200% of $D_1$. Second section 114 (e.g., the distal half) may have an outer diameter that decreases from diameter $D_2$ to an outer diameter approximately equal to $D_1$. According to the rate at which the first sections diameter increases and the rate at which the second sections diameter decreases, the distal portion includes a cross-sectional profile (along the longitudinal axis) that has a snakehead-like shape, parabolic shape, arcuate shape, semi-circular shape, trapezoidal shape, or the like. According to other embodiments, the distal portion includes a cross-sectional profile with alternative shapes.

Regardless of the shape created, first section 112 and second section 114 create an area on the distal end portion 110 with an increased diameter $D_2$ that is located a proximal distance from distal tip 116. As further described below, by having a portion of the optical fiber with an increased diameter set back from the distal tip, contact between the distal tip and a channel in an endoscope or catheter may be avoided.

According to embodiments, the distal tip 116 of the optical fiber may include a curved portion 117 and a planar portion 118. Curved portion 118 may include the outer edge/rim of the distal end portion 110 of optical fiber 100, while planar portion 118 may generally include the distal end face of optical fiber 100. The curved portion 117 in combination with the planar portion 118 may be shaped such that distal tip 116 does not include any sharp edges/corners (e.g., is completely smooth). According to alternative embodiments, distal tip 116 of optical fiber 100 may include a substantially curved or flat surface. According to further embodiments, distal tip 116 may take other shapes.

As illustrated by FIGS. 1 and 2, the dimensions and shape of first section 112, second section 114, and distal tip 116 are such that distal end portion 110 of optical fiber 100 includes a thickened area that is located a distance from the distal tip, creating a distal end with a snakehead-like shape.

According to embodiments, methods of manufacturing optical fiber 100 include a first step of creating and preparing a preform. The preform may be made from silica or silica composites. According to preferred embodiments, the preform is made of pure silica. A second step may include subjecting the preform to a drawing process. According to embodiments, the cladding is applied during the drawing process, such that cladding is coated onto the resulting core of the optical fiber. The cladding may be made from silica or silica composites, for example, silicone or a hard-clad material. According to preferred embodiments, the cladding is an all-silica cladding. During the drawing process a coating may also be applied. As a result of these steps a central core is created, which is surrounded by a cladding. According to preferred embodiments, the core and cladding consist of pure silica. The cladding is further surrounded by the coating. A third step may include extruding the resulting fiber with a buffer.

A fourth step may comprise disposing or depositing a jacket on the coating. According to embodiments, the jacket may be coated onto coating. According to alternative embodiments, the jacket may be co-extruded with the core, cladding, and/or coating. The jacket may be made from a thermoplastic polymer (e.g., nylon, or ETFE). According to embodiments, the jacket is optional and optical fiber 100 may omit such a jacket.

The above method of manufacturing optical fiber 100 is meant to be illustrative, and alternative methods of manufacturing optical fiber 100 are within the scope of this disclosure. For example, materials selected for use as the core, cladding, coating, and jacket may be modified. Similarly, different methods of forming each of the core, cladding, coating, and jacket, as well as how each are formed to one another, are within the scope of this disclosure.

With optical fiber 100 formed, methods of modifying distal end 110 will now be described. The method of modifying distal end 110 may include heating a distal end of the optical fiber with a heating element, for example, an arc lamp. Heat from the heating element may be configured to deform the distal end at the locations of the first section 112 and second section 114. The heat may be varied across the distal end of the optical fiber to create a snakehead-like shape. According to embodiments, the heating element is brought in close proximity to the distal end of the optical fiber. The optical fiber may then undergo controlled rotation and/or movement so that the distal end deforms (e.g., due to melting and surface tension properties). According to alternative embodiments, pressure may be applied to the distal end of the optical fiber (e.g., during a manufacturing process) in order to deform the distal end.

The above method allows for modifying a continuous optical fiber, as compared to traditional modifications that require the splicing of discrete fiber pieces together. Such a method advantageously maintains a unitary construction, which is more stable and cheaper to manufacture.

According to further embodiments, a capillary ring may be attached to the distal end of the optical fiber in order to form the modified shape.

In accordance with an aspect of an illustrative embodiment of the present disclosure, optical fiber 100, having a snakehead-like shaped distal end portion 110, may be associated with a catheter or endoscope for use in a urology procedure. The procedure may include feeding the endoscope or catheter into the body of a patient, for example, by way of a guide wire such that the endoscope or catheter is located proximate to a renal stone. Optical fiber may be fed through the endoscope or catheter such that distal tip 116 of optical fiber 100 is also located proximate to the rental or bladder stone.

Due to the snakehead-like shape of distal end portion 110, and in particular the increased outer diameter of at least portions of first section 112 and second section 114 as described above, when optical fiber 100 is fed through a channel in the endoscope these increased outer diameter portions make contact with the inner lumen of the channel. Because of the increased outer diameter of at least portions of first section 112 and second section 114, distal tip 116, with an outer diameter less than portions of first section 112 and second section 114, is less likely to make contact with the inner lumen of the channel. By preventing distal tip 116 from contacting the inner lumen of the channel, distal tip 116 is less likely to be damaged as it is fed to a desired location. The increased diameter of at least portions of first section 112 and second section 114 also increases the overall stability of optical fiber 100 during the feeding process.

An energy source (e.g., a holmium laser) may be coupled to the proximal end of optical fiber 100. When the energy source is activated, light from the energy source travels through the optical fiber and is focused onto the stone. The focused energy is directed onto the stone in order to break the stone into smaller pieces or cause the stone to disintegrate. The smaller pieces may then be removed by known means.

Additionally, due to the snakehead shape of distal end portion 110 the beam profile may be concentrated (e.g., focused) to a higher degree, as compared to traditional flat tip optical fibers. For example, as illustrated by FIG. 2a, the beam generated by the energy source is focused as it exits distal tip 116.

Figure 3:
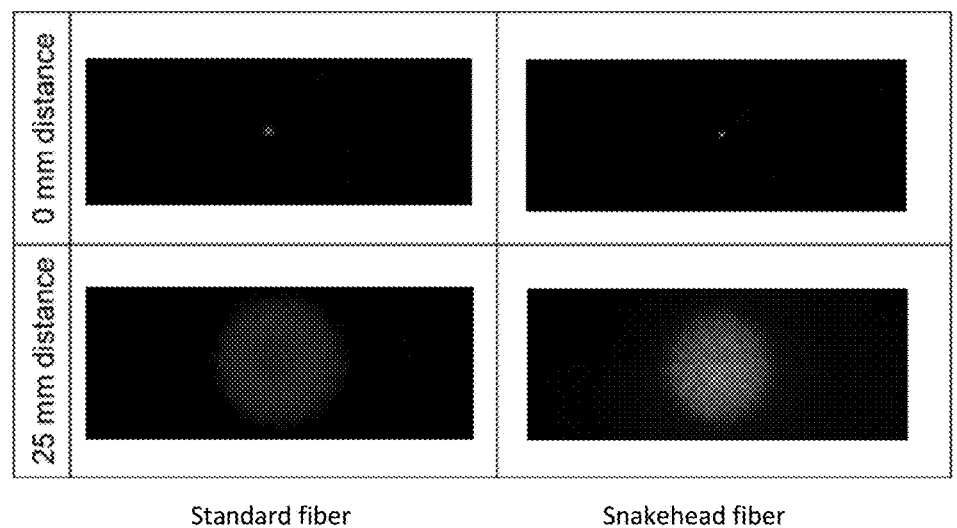
FIG. 3 illustrates beam profiles created by a standard optical fiber and an optical fiber of the present disclosure at 0 mm and at 25 mm distances.

As further evidence of this focusing, FIG. 3 illustrates the beam profile created at 0 mm and 25 mm from a standard fiber and from a fiber including a snakehead-shaped distal end according to the present disclosure. When comparing the beam profile of a standard fiber to a fiber of present disclosure, it is evident that the light exiting the distal tip 116 of a fiber of present disclosure is more concentrated and generates less scattering. By focusing the beam generated by the energy source, the optical fiber of the present invention advantageously prevents unwanted scattering and reduces the likelihood that radiation impinges upon unwanted targets.

The above methods of implementing and using optical fiber 100 is meant to be illustrative, and alternative methods of implementing and using optical fiber 100 are within the scope of this disclosure. For example, optical fiber 100 may be used in other medical procedures where an optical fiber is fed through an endoscope or catheter. It is also possible to use optical fiber 100 without an endoscope or catheter (e.g., the fiber may be directly fed into a body vessel).

What is claimed is:

1. An optical fiber, comprising:
a core; and
a cladding disposed on the core;
wherein the optical fiber extends from a distal portion to a proximal portion along a longitudinal axis of the optical fiber, and
wherein the distal portion comprises:
a first section;
a second section; and
a distal tip,
wherein the first section extends lengthwise along the longitudinal axis between the proximal portion and the second section, the second section extends from the first section lengthwise between the first section and the distal tip, and the proximal portion has an outer diameter, $D_1$, that is substantially constant over a length of the proximal portion along the longitudinal axis greater than a length along the longitudinal axis extending over the first section, the second section, and the distal tip, and
wherein at least one of the first section and the second section comprises a maximal outer diameter, $D_2$, of the distal portion that is greater than the outer diameter, $D_1$, of the proximal portion and is greater than the outer diameter of the distal tip;
wherein the distal tip comprises a curved portion and a planar portion, the planar portion being orthogonal to the longitudinal axis of the optical fiber and comprising an end face of the optical fiber, the curved portion extending from the planar portion to the second section and having a magnitude of curvature different from a magnitude of curvature of a portion of the second section that extends from and is adjacent to the curved portion; and
wherein the optical fiber is configured such that when light is coupled into the optical fiber via the proximal position, the light is guided through the core along the longitudinal axis toward the distal portion and is focused as the light exits the planar portion of the distal tip, the light emitted from the distal tip thereby being concentrated.

2. The optical fiber of claim 1,
wherein the first section has an outer diameter that increases along at least a part of its length, along the longitudinal axis, from the proximal portion to the second section.

3. The optical fiber of claim 2,
wherein the second section has an outer diameter that decreases along at least a part of its length, along the longitudinal axis, from the first section to the distal tip.

4. The optical fiber of claim 3,
wherein the increase in the outer diameter along the longitudinal axis of the first section results in the maximal outer diameter $D_2$.

5. The optical fiber of claim 4,
wherein the first section comprises:
a first portion, the first portion having an outer diameter that increases, along its length along the longitudinal axis, from $D_1$ to $D_2$; and
a second portion extending from the first portion along a given length of the longitudinal axis, the second portion having an outer diameter of $D_2$ that remains constant along the given length of the second portion.

6. The optical fiber of claim 4,
wherein the outer diameter increases at a constant rate along the length of the first section.

7. The optical fiber of claim 4,
wherein the outer diameter increases at a non-constant rate along the length of the first section.

8. The optical fiber of claim 4,
wherein the second section has a maximum outer diameter equal to $D_2$, and
wherein the decrease in diameter along the longitudinal axis of the second section includes a decrease from $D_2$ to approximately $D_1$.

9. The optical fiber of claim 8,
wherein the second section comprises:
a first portion extending along a given length of the longitudinal axis, the first portion having an outer diameter that is equal to $D_2$ and is constant along the given length of the first portion; and
a second portion, the second portion extending from the first portion along the longitudinal axis and having an outer diameter that decreases from $D_2$ to $D_1$.

10. The optical fiber of claim 8,
wherein the outer diameter decreases at a constant rate along the length of second section.

11. The optical fiber of claim 8,
wherein the outer diameter decreases at a non-constant rate along the length of second section.

12. The optical fiber of claim 8, wherein the second section comprises:
a first portion having an outer diameter that decreases from $D_2$ to approximately $D_1$ along the longitudinal axis in a direction from the first section to the distal tip; and
a second portion extending from the first portion along a given length of the longitudinal axis between the first portion and the distal tip and having an outer diameter of approximately $D_1$ along the entire given length.

13. The optical fiber of claim 4,
wherein the first section and the second section together form an arcuate, semicircular, or parabolic shape along an edge of the optical fiber in a longitudinal cross-section, and
wherein portions of the first section and the second section with diameter $D_2$ are located a proximal distance from the distal tip.

14. The optical fiber of claim 4,
wherein the first section and the second section together form a trapezoidal-like shape along an edge of the optical fiber in a longitudinal cross-section, and
wherein portions of the first section and the second section with diameter $D_2$ are located a proximal distance from the distal tip.

15. The optical fiber of claim 4, wherein $D_2$ is approximately equal to 120% to 200% of $D_1$.

16. The optical fiber of claim 1,
wherein the second section is located a distance proximally from the distal tip.

17. The optical fiber of claim 1,
further comprising a coating disposed on the cladding, wherein the coating comprises silicone.

18. The optical fiber of claim 17,
further comprising a jacket disposed on the coating, wherein the jacket comprises a thermoplastic polymer.

19. The optical fiber of claim 1,
wherein the distal tip comprises a curved or semicircular shape.

20. The optical fiber of claim 1,
wherein the distal portion of the optical fiber is configured to cause the light that travels therethrough and exits out of the planar portion of the distal tip to be focused to a higher degree compared to a flat tip optical fiber having a constant diameter of approximately $D_1$.

21. The optical fiber of claim 1, wherein the curved portion and the planar portion are configured such that the distal tip does not include sharp edges.

22. The optical fiber of claim 1, wherein the distal tip includes a curved portion having a magnitude of curvature greater than a magnitude of curvature of a portion of the second section that extends from and is adjacent to the distal tip.

23. The optical fiber of claim 1, wherein the second section comprises:
a first portion having a first length extending along the longitudinal axis, and having an outer diameter that is constant along the first length; and
a second portion having a second length extending along the longitudinal axis, and having an outer diameter that decreases along the second length in a direction from the first portion to the distal tip.

24. The optical fiber of claim 1, wherein the second section has an outer diameter that is constant along its length between the first section and the distal tip and is approximately equal to $D_2$.

25. A method of performing a urology procedure, the method comprising:
inserting an endoscope or catheter through a vessel lumen of a patient,
feeding the endoscope or catheter through the vessel until a distal end of the endoscope or catheter is located proximate to a renal or bladder stone;
inserting an optical fiber as recited in claim 1 into a channel located within the endoscope or catheter, and
feeding the optical fiber through the channel located within the endoscope or catheter until the distal tip of the optical fiber is located proximate to the renal or bladder stone, wherein the section of the distal portion having a larger outer diameter contacts an inner wall of the channel and prevents the distal tip from contacting the inner wall.

26. The method of claim 25, further comprising: coupling an energy source to the proximal portion of the optical fiber; activating the energy source, wherein the activation causes light to: enter the optical fiber via the proximal portion; exit via the distal tip; and impinge upon the renal or bladder stone; wherein the shape of the optical fiber is configured to focus the light as it passes there through.

27. The method of claim 26, wherein energy from the light impinging upon the renal or bladder stone causes the renal or bladder stone to break apart.

28. An optical fiber, comprising:
a core; and
a cladding disposed on the core;
wherein the optical fiber extends from a distal portion to a proximal portion along a longitudinal axis of the optical fiber, and
wherein the distal portion comprises:
a first section;
a second section; and
a distal tip,
wherein the first section extends lengthwise along the longitudinal axis between the proximal portion and the second section, the second section extends from the first section lengthwise between the first section and the distal tip, and the proximal portion has an outer diameter, $D_1$, that is substantially constant over a length of the proximal portion along the longitudinal axis greater than a length along the longitudinal axis extending over the first section, the second section, and the distal tip,
wherein at least one of the first section and the second section comprises a maximal outer diameter, $D_2$, of the distal portion that is greater than the outer diameter, $D_1$, of the proximal portion and is greater than the outer diameter of the distal tip,
wherein the first section has an outer diameter that increases along at least a part of its length, along the longitudinal axis, from the proximal portion to the second section, to result in the maximal outer diameter $D_2$, and
wherein the second section has (i) an outer diameter that decreases along at least a part of its length, along the longitudinal axis, from the first section to the distal tip, and (ii) a maximum outer diameter equal to $D_2$, wherein the decrease in diameter along the longitudinal axis of the second section includes a decrease from $D_2$ to approximately $D_1$, and wherein the second section comprises:
a first portion having an outer diameter that decreases from $D_2$ to approximately $D_1$ along the longitudinal axis in a direction from the first section to the distal tip; and
a second portion extending from the first portion along a given length of the longitudinal axis between the first portion and the distal tip and having an outer diameter of approximately $D_1$ along the entire given length.

29. A method of performing a urology procedure, the method comprising:
inserting an endoscope or catheter through a vessel lumen of a patient,
feeding the endoscope or catheter through the vessel until a distal end of the endoscope or catheter is located proximate to a renal or bladder stone;
inserting an optical fiber as recited in claim 28 into a channel located within the endoscope or catheter, and
feeding the optical fiber through the channel located within the endoscope or catheter until the distal tip of the optical fiber is located proximate to the renal or bladder stone, wherein the section of the distal portion having a larger outer diameter contacts an inner wall of the channel and prevents the distal tip from contacting the inner wall.

30. The method of claim 29, further comprising: coupling an energy source to the proximal portion of the optical fiber; activating the energy source, wherein the activation causes light to: enter the optical fiber via the proximal portion; exit via the distal tip; and impinge upon the renal or bladder stone; wherein the shape of the optical fiber is configured to focus the light as it passes there through.

31. The method of claim 30, wherein energy from the light impinging upon the renal or bladder stone causes the renal or bladder stone to break apart.

* * * * *